United States Patent [19]

Linkow et al.

[11] Patent Number: 4,915,628

[45] Date of Patent: Apr. 10, 1990

[54] SUBMERGIBLE DENTAL IMPLANT AND METHOD OF UTILIZATION

[75] Inventors: Leonard I. Linkow, New York, N.Y.; Anthony W. Rinaldi, Philadelphia, Pa.

[73] Assignee: Vent-Plant Corporation, Inc., Philadelphia, Pa.

[21] Appl. No.: 284,235

[22] Filed: Dec. 14, 1988

[51] Int. Cl.$^4$ .............................................. A61C 8/00
[52] U.S. Cl. .................................................... 433/173
[58] Field of Search ................ 433/173, 174, 225, 165

[56] References Cited

U.S. PATENT DOCUMENTS 2,449,522  9/1948  White .................................... 433/175

Primary Examiner—Robert Peshock
Attorney, Agent, or Firm—Darby & Darby

[57] ABSTRACT

An implant portion of an oral implant arrangement for supporting an artificial tooth structure has an elongated body having a first and a second ends. The first end is adapted to receive at least a portion of the artificial tooth structure. The second end is adapted for insertion into a crypt in a bone located to support the artificial tooth in the vicinity of the occlusal plane of a patient. At least one longitudinal column projecting outwardly from the outside surface of the elongated body and extending at least part way toward the second end of the body is provided. A cutting arrangement is defined at the end of the longitudinal column toward the second end of the body. During insertion of said elongated body into the crypt in the bone the longitudinal column closely engages slots formed within the walls of the bone crypt by the cutting arrangement so as to create at least one antirotational pillar which resist accidental spinning of the implant portion in the crypt.

19 Claims, 2 Drawing Sheets

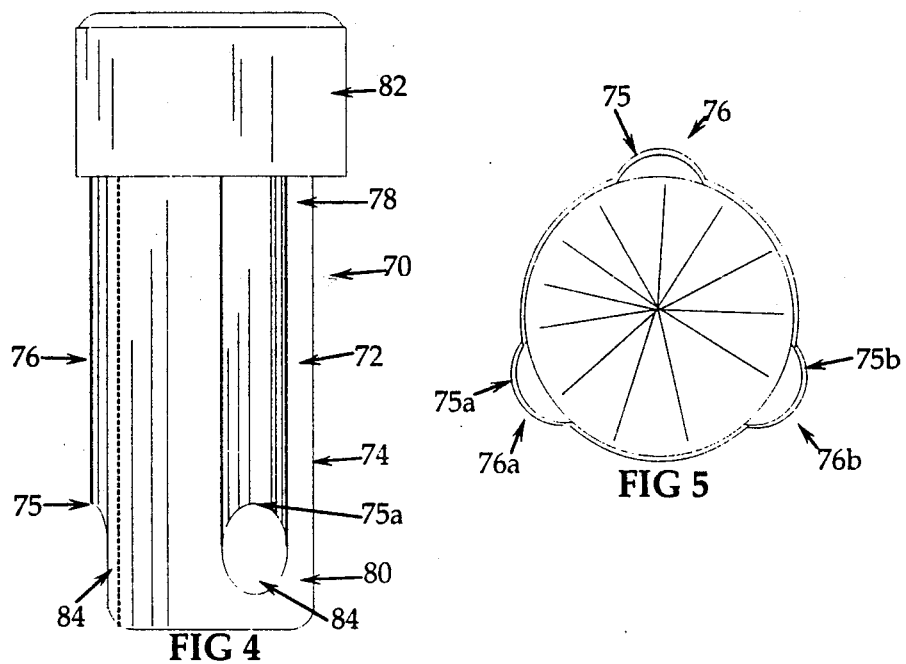

SUBMERGIBLE DENTAL IMPLANT AND METHOD OF UTILIZATION

BACKGROUND OF THE INVENTION

This invention relates to dental implants, and more particularly to submergible implants.

Submergible cylindrical threaded dental implants, which are placed in a cylindrical hole in an edentulous area along the dental bone of a patient, are used to support an artificial tooth structure. After being allowed to heal in place, the implant receives a transmucosal post. The most common method for the subsequent attachment of the transmucosal post or abutment to the healed implant is by standard screw threads. However, the torque required for tightening of a threaded abutment may occasionally spin the implant in its bony crypt.

This spinning can occur when there is a poor healing environment, i.e. excessive amounts of fibrous tissues are present at the place of connection between the bone and implant. The effect of this turning of the implant is to cause irreversible damage at the implant-to-bone interface, and implant failure.

U.S. Pat. No. 4,713,004 issued to the present applicants illustrates a submergible screw-type implant utilizing longitudinal channels which direct bone chips towards the base of a hole in the patients bone during threading of the implant into the hole in the bone. These chips pass through a plurality of vents in the implant body and into a central chamber of the implant where they promote autogenous rapid regrowth of new bone to securely anchor the implant in place. This implant, however, is free to rotate during the subsequent abutment connection. This rotation might lead to the failure of the implant.

SUMMARY OF THE INVENTION

The present invention provides an implant portion of an oral implant arrangement for supporting an artificial tooth structure in which the implant portion is arranged in the hole in the bone in such a way that it does not rotate.

In an illustrative embodiment of the invention the implant portion is a cylindrical body with at least one longitudinal column protruding from the outer surface of the body and extending from an upper portion of the implant body part way toward its bottom end. An opening from an outside surface of the body into an internal chamber is provided below the column. A cutting means is arranged at the lower end of the column.

During insertion of the implant into a crypt or hole in the bone which closely matches the diameter of the implant body, the cutting means at the bottom of the column cuts into the surrounding bone and produces bone chips which are transferred through the opening into the internal chamber of the implant to promote autogenous rapid bone regrowth. The column engages the slots in the bone formed by pushing the implant cutter into the bone and acts as an antirotation pillar.

The crypt for the implant of the present invention may be formed with a bone notch cutter. This cutter has a hollow body with a receiving member which is positioned at one end. At least one portion projects outwardly from an outside surface of the body of the cutter. A blade arrangement is defined at face end of the projected portion for cutting into the bone during insertion in a predrilled hole.

BRIEF DESCRIPTION OF THE DRAWINGS

Other advantages and features of the invention are described with reference to exemplary embodiments, which are intended to explain and not to limit the invention, and are illustrated in the drawings in which:

FIG. 4 is a side view of a notch cutter according to the present invention.

FIG. 5 is a bottom plan view of the notch cutter of FIG. 4.

DESCRIPTION OF ILLUSTRATIVE EMBODIMENTS

Although a specific embodiment of the invention will now be described with reference to the drawings, it should be understood that the embodiment shown is by way of example only and merely illustrative of but one of the many possible specific embodiments which can represent applications of the principles of the invention. Various changes and modifications, obvious to one skilled in the art to which the invention pertains, are deemed to be within the spirit, scope and contemplation of the invention as further defined in the appended claims.

Figure 1:
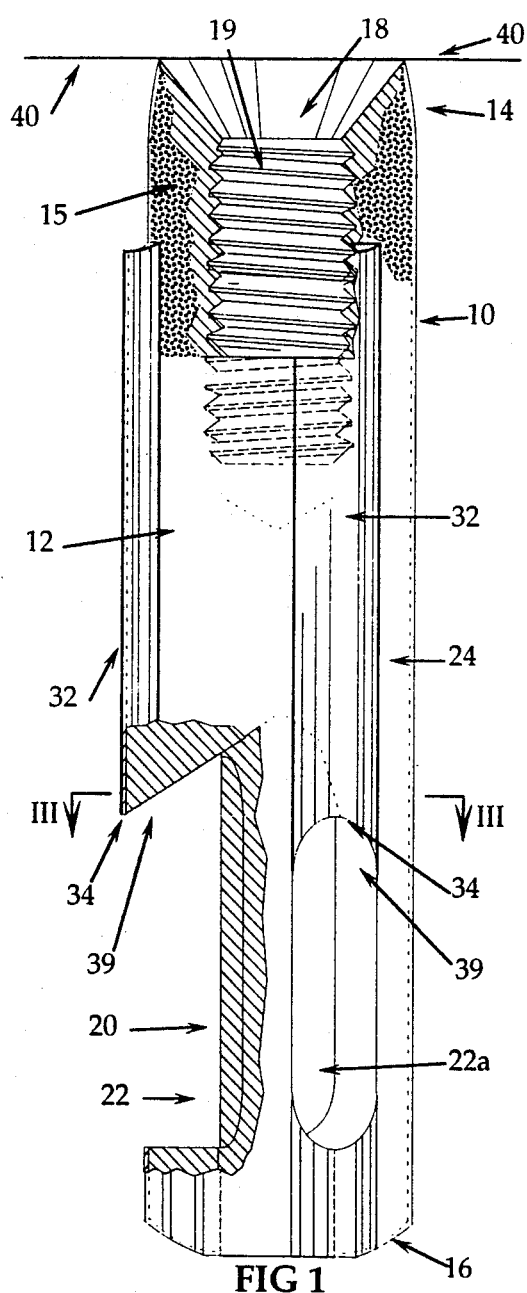
FIG. 1 is a side view, partially in section, of a non-threaded implant according to the present invention.
Figure 3:
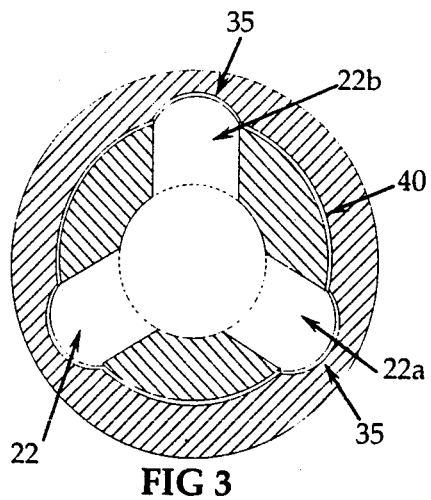
FIG. 3 is a cross-sectional view of the implant of FIG. 1 along line 3—3 as inserted into the bone crypt.
Figure 2:
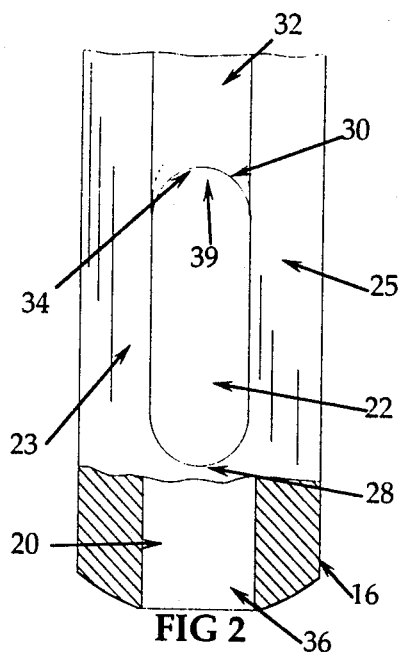
FIG. 2 is a broken side view, partially in section, of a lower part of another embodiment of the implant of the present invention.

In FIGS. 1, 2, and 3, a non-threaded implant portion 10 is illustrated. The implant portion shown in these figures has an elongated body 12. The body 12 has a first end 14 and a second end 16. The first end is provided with a receiving arrangement 18 which is adapted to receive a post or abutment portion which supports an artificial tooth structure. The second end 16 is designed for insertion into a crypt formed in alveolar ridge crest bone of a patient in an edentulous area so as to support an artificial tooth in the vicinity of the occlusal plane of the patient. An internal cavity 20 is provided within the body near the second end 16. Spaced from the second end 16 are holes or vents 22, 22a and 22b in the wall 24 of the body. FIG. 3 shows the implant having three vents symmetrically disposed within the column. However, any reasonable number of vents is possible. The vents penetrate from the outside wall 24 of the body into the internal cavity 20. One of the purposes of these vents is to allow new bone to grow through and into the center of the cavity in order to firmly enclose the implant in the patient's bone.

The receiving arrangement 18 of the first end has a threaded aperture 19 which is used to connect the abutment (not shown) to the implant portion or to receive directly an artificial dental structure.

The vents 22 shown in FIGS. 1 and 2 have an elongated configuration. Each vent is defined by side walls 23 and 25 and has two rounded ends 28 and 30. The end 28 is positioned in the vicinity of the second end 16 of the elongated body. The rounded end 30 is situated opposite the end 28.

The elongated body 12 is provided with at least one longitudinal column 32 which projects outwardly from its outside surface 24. The longitudinal column 32 extends in a direction substantially parallel to the longitudinal axis of the body 12 and typically has an arch-shaped cross-sectional configuration as shown in FIG. 3. A cutting means or arrangement 34 can be positioned at the intersection between the end 30 of each vent and the longitudinal column 32. In the embodiment of FIG. 1, it is shown that the cutting arrangement is formed with sharp edges 34 positioned at the outer edge of the intersection of the longitudinal columns 32 and the ends 30 of the vents. As shown in FIG. 3 there are three antirotational columns with cutters at each end. The columns are evenly spaced at 120° positions. However, other numbers or columns and/or spacing may be used.

In certain situations when a notch cutter (discussed herein below) is used to create antirotational slots in the bone crypt, the longitudinal columns can be manufactured without the cutting arrangement.

The second end 16 of the elongated body can be rounded and solid as shown in FIG. 1. FIG. 2 illustrates an embodiment of the invention having an opening 36 located at the second end 16 and connecting the exterior of the column with the internal cavity 20. The opening 36 facilitates the insertion of the column into the bone crypt by reducing hydrostatic pressure during the insertion which could be caused by blood which has collected in the crypt. The opening 36 also allows this blood to enter the internal cavity 20 to mix with autogenous bone cutting to enhance growth of new bone to anchor the implant.

During installation of the implant into the bone crypt, an incision is made in the gum tissue and the underlying bone is exposed. Then, a drill or burr is used to make an initial cylindrical crypt in the bone 40 which is slightly larger in diameter then the diameter of the longitudinal body of the implant portion. If the receiving portion is larger than the rest of the body, another drill is used to widen the crypt near the bone surface.

Next, in dense cortical bone, such as in the symphysis area of the mandible, it may be necessary to use an antirotational notch cutter 70 illustrated in FIGS. 4 and 5. The notch cutter 70 is used to prepare at least partially antirotational slots through the dense superior cortical plate of a bone.

The notch cutter 70 comprises a hollow, substantially cylindrical body 72 having a diameter slightly smaller than the diameter of the cylindrical bone crypt. The body 72 is provided with a first end 78 and a second end 80. There is at least one column-like projection 76 extending outwardly from an outside surface 74 of the body. FIG. 5 illustrates three elongated projections 76, 76a and 76b which are disposed circumferentially about the body 72 to match the columns 32 of implant of FIG. 1. However, any reasonable number of projections is possible. Each projection has a corresponding sharp cutting edge 75, 75a, 75b positioned in the vicinity of the second end 80 of the body. Holes 84, which penetrate through the wall of the hollow body to its interior are positioned between the cutting edges and the second end 80.

A solid member 82 is attached to the first end 78 of the body and is adapted to receive the force of a surgical mallet or similar tool which strikes the notch cutter. The second end 80 is free.

During operation, a substantially cylindrical second end 80 is inserted into the previously prepared bone crypt as a guide. Then, when the surgical mallet is used to strike the member 82, the cutting edges 75, 75a and 75b cut longitudinal grooves within a side wall of the crypt. The bone cuttings developed during this procedure collect at the bottom of the crypt and can be conveniently utilized when the implant having the opening 36 at the second end of the longitudinal column (see FIG. 2) is used.

The notch cutter can be used the produce the initial antirotational slots only within the dense area of the bone crypt near the occlusal plane or to produce the antirotational slots through the entire length of the crypt.

Once the antirotational slots passing through the whole length of the crypt have been prepared by the notch cutter 70, the implant portion 10 can be inserted into the bone crypt. The inside dimensions of the initial antirotational slots are slightly smaller than the outside dimensions of the longitudinal columns 32. Therefore, when the elongated body 12 is inserted into the bone crypt, the longitudinal columns 32 follow the initial antirotational slots in such a manner that the sharp cutting edges 34 produce additional bone chips which are directed through the vents into the internal cavity 20 of the column. However, the longitudinal columns without the cutting edges also can be used.

If the notch cutter 70 is used to produce only the initial antirotational slots within the area of the bone crypt near the occlusal plane, the length of the slots can be subsequently extended throughout the crypt during insertion of the implant portion having the longitudinal columns with the cutting edges. In this case the extension of the antirotational slots is produced by the cutting edges which follow the initial slots.

It is illustrated in FIG. 3 that when the elongated body 12 is fully inserted into the bone crypt, the longitudinal columns 32 are closely received by the antirotational slots 35, thereby fixing the position of the elongated body within the crypt. Also, as shown in FIG. 1, the upper end of the implant is slightly below the bone crypt 40 and therefore is considered a submergible implant. However, the present invention is also useful with implants that extend above the bone line.

The engagement between the slots 35 and the longitudinal columns 32 creates antirotational pillars which resist accidental spinning of the implant when an artificial tooth support or abutment is threaded into aperture 19. This is the case whether the implant has healed in place or has been freshly installed.

Bone chips created during the implant procedure tend to accumulate at the base of the implant portion in the patient's bone and within the internal cavity 20 of the implant. Because of the autogenous nature of these bone chips, they tend to promote the rapid growth of a new bone around and through the implant such that it is enclosed in place more rapidly. This may be allowed to occur by covering the implant with gum tissue without install abutment and keeping the implant out of service for several weeks while it heals. The tissue may later be opened and the abutment threaded onto the implant.

In certain situations, use of the notch cutter 70 may not be necessary to produce the initial antirotational slots in the bone crypt. In such a case, after the initial cylindrical crypt having a diameter slightly larger than the diameter of the implant is drilled in the bone, the second end 16 of the longitudinal column is inserted into the crypt. Then, the force is applied to the first end 14 of the implant and the cutting edges 34 cut the longitudinal grooves within the wall of the crypt. Such grooves are deep enough to closely receive the longitudinal columns of the implant. Similar to the above discussed embodiment, the engagement between the slots within the bone crypt and the longitudinal columns create the antirotational pillars prevent accidental spinning of the implant. Bone chips created during the insertion of the implant are also used to promote new bone growth.

To facilitate growing together of the implant and the bone, and to minimize the possibility of rejection of the implant by the human body, at least a part of the outside surface of the implant portion can be made of or coated with a biocompatible material having a rough surface texture or a porous coating 15. To create such an irregular surface for bone ingrowth, the outside surface of the implant can be coated with titanium flame plasma spray, hydroxylapatite plasma spray or other means for creating irregular surfaces.

What is claimed is:

1. An implant portion of an oral implant arrangement for supporting an artificial tooth structure, comprising
   an elongated body having a first and a second ends, said first end being adapted to receive at least a portion of said artificial tooth structure, said second end being adapted for insertion into a crypt in a bone located to support the artificial tooth in the vicinity of the occlusal plane of a patient,
   at least one longitudinal column projecting outwardly from said outside surface of the elongated body and extending at least part way toward the second end of the body,
   cutting means defined at the end of said longitudinal column toward the second end of said body,
   whereby during insertion of said elongated body into the crypt in the bone said longitudinal column closely engages slots formed within the walls of the bone crypt by the cutting means so as to create at least one antirotational pillar which resist accidental spinning of the implant portion in the crypt.

2. An implant portion according to claim 1, further comprising an internal chamber within said elongated body, at least one opening through said body from an outside surface thereof to said internal chamber, and wherein said cutting means during insertion produces bone chips which are transferred through said opening into said internal chamber to promote autogenous rapid new bone regrowth to anchor the implant portion in place.

3. An implant portion according to claim 2, wherein said internal chamber extends through the second end of the body in such a manner that an aperture is defined at said second end connecting said outside surface of the body with the internal chamber; and wherein said aperture reduces hydrostatic pressure during the insertion of the implant into the bone crypt and allows additional blood to enter the internal chamber and to mix with the autogenous bone chips.

4. An implant portion according to claim 2, wherein said elongated body has a substantially cylindrical configuration.

5. An implant portion according to claim 2, further including a plurality of said openings located over the circumference of the column.

6. An implant portion according to claim 1, wherein a receiving means is provided within the first end of the body of the elongated body to receive a portion of the artificial tooth structure.

7. An implant portion according to claim 6, wherein said receiving means is a threaded aperture.

8. An implant portion according to claim 2, wherein at least a portion of the outside part of said elongated body has a rough and porous surface.

9. An implant portion according to claim 8, wherein said rough and porous surface of the outside part is made of a bio-compatible material.

10. An implant portion according to claim 2, wherein said cutting means is a sharp edge defined at the intersection of said opening and said longitudinal column.

11. A bone notch cutter, comprising a hollow body having first end and a second end, a receiving member positioned at said first end, said second end being free, at least one longitudinal projecting portion projecting outwardly from an outside surface of said body, said projecting portion having a free end located in the vicinity of said second end of the body, and cutting means defined at said free end of the projecting portion.

12. A bone notch cutter according to claim 11 wherein an aperture through said hollow body is positioned between said free end of the projecting portion and said second end of the body.

13. A bone notch cutter according to claim 11, wherein said outside surface of the hollow body has a substantially cylindrical configuration.

14. A bone notch cutter according to claim 13, further including a plurality of said projecting portions disposed circumferentially about said hollow body.

15. A bone notch cutter according to claim 11, wherein said cutting means is a sharp edge.

16. A bone notch cutter according to claim 11, wherein said receiving means is a solid member.

17. A bone notch cutter according to claim 11, wherein said projecting portion has an arc-shaped cross-section.

18. A bone notch cutter according to claim 12, wherein said bone notch cutter is adapted to produce at least one antirotational slot through a dense superior cortical plate of a bone after an initial substantially cylindrical crypt is prepared in such a manner that an implant inserted into the crypt and tapped into place utilizes said antirotational slot while bone chips produced by said notch cutter are directed toward a base of the bone crypt.

19. A bone notch cutter according to claim 17, wherein a diameter of said hollow body is smaller than the diameter of the substantially cylindrical crypt and said receiving member is adapted to receive a force pushing said notch cutter within the crypt to produce said slot.

* * * * *